United States Patent [19]

Schneider

[11] Patent Number: 5,731,290
[45] Date of Patent: Mar. 24, 1998

[54] METHOD OF IMPROVING THE IMMUNE RESPONSE

[75] Inventor: Heinz Schneider, Cordast, Switzerland

[73] Assignee: Novartis Corporation, Summit, N.J.

[21] Appl. No.: 394,872

[22] Filed: Feb. 27, 1995

[51] Int. Cl.⁶ .......................... A61K 38/00; A01N 43/04
[52] U.S. Cl. ........................ 514/20; 514/21; 514/42; 514/44; 514/45; 514/46; 514/47; 514/48; 514/49; 514/50; 514/51; 514/561; 514/564; 514/784
[58] Field of Search ..................... 514/21, 20, 42, 514/44, 45, 46, 47, 48, 49, 50, 51, 784, 561, 564

[56] References Cited

U.S. PATENT DOCUMENTS

| | | | |
|---|---|---|---|
| 4,752,618 | 6/1988 | Mascioli et al. | 514/549 |
| 5,231,085 | 7/1993 | Alexander et al. | 514/44 |

FOREIGN PATENT DOCUMENTS

| | | |
|---|---|---|
| 0367724 | 5/1990 | European Pat. Off. . |
| 0567433 | 10/1993 | European Pat. Off. . |

*Primary Examiner*—Nathan M. Nutter
*Attorney, Agent, or Firm*—Michael P. Morris; Carl W. Battle

[57] ABSTRACT

The invention provides diet supplements for pre-operative treatment of patients due for surgery.

10 Claims, No Drawings

METHOD OF IMPROVING THE IMMUNE RESPONSE

It is known that it is possible to enhance the recovery of a deficient or suppressed immune function by diet. Typical examples of immunostimulatory diets are complete diets (i.e. diets supplying essentially all required energy, amino acids, vitamins, minerals and trace elements) comprising arginine, RNA, omega-3 and omega-6 polyunsaturated fatty acids (PUFAs).

Major surgeries affect the immune response system and increase the risk of post-operative infection of patients having undergone surgery.

It would now be advantageous if it were possible to prepare, by diet, the immune system of a patient due for surgery such that his/her immune response and/or the resistance to infection is improved upon surgery.

It has now been found that it is possible to improve the immune response and/or the resistance to infection upon surgery by administering to patients prior to surgery a dietary supplement comprising an immunostimulatory effective aggregate amount of (a) omega-3 polyunsaturated fatty acids (PUFAs) and (b) L-arginine, L-ornithine, an L-arginine or L-ornithine precursor, or a mixture thereof.

The improved immune response and increased resistance to infection upon surgery after pre-operative treatment with components (a) and (b) may be illustrated by tests.

Examples of tests suitable to indicate that the desired effect has been obtained include i.a. the determination of the docosahexaenoic (DHA) and eicosapentaenoic acid (EPA) content of blood serum and of tissues such as liver tissue, the intestinal mucosa and tumor tissue at the operative day, determination of parameters characteristic for the activity of neutrophils, determination of parameters indicating activation of the immune system cells and the like.

The results are compared with results obtained after treatment of patients with a standard supplement. A favourable effect is indicated if for example the serum lipid DHA and/or EPA content is increased. An increase of LTB 5 and a decrease of LTB 4 and LTC 4 upon surgery indicates that the activity of the neutrophils is improved. Activation of the immune system cells upon surgery is i.a. illustrated by a reduced decrease in IL-1α (an activator of immune cells), a reduced decrease in activated T-cells (as established by CD 3 and HLA-DR-determination), a reduced decrease in differentiated suppressor T-cells (as established by CD 8 determination) and a reduced decrease in NK-cells. Experiments suggest that the desired effect can be attained after pre-operative treatment of patients with components (a) and (b).

The invention therefore provides a dietary supplement comprising an immunostimulatory effective aggregate amount of component (a) and component (b).

The present invention further provides a method of improving the immune response and/or resistance to infection of a patient following surgery comprising treating said patient pre-operatively with a diet supplement containing an immunostimulating effective aggregate amount of component (a) and component (b).

The invention also provides the use of component (a) and of component (b) in the manufacture of an immunostimulatory pre-operative diet for post-operative stimulation of the immune system of patients subject to surgery.

For the purpose of the invention omega-3 PUFAs may be in free acid form or in a form suitable for the physiological supply of omega-3 PUFAs, e.g. in triglyceride form. Examples of omega-3 PUFAs particularly appropriate for use in the compositions of the invention include (EPA) and (DHA). Suitable sources for such omega-3 PUFAs are known. They include linseed oil and fish oils such as menhaden oil, salmon oil, mackeral oil, tuna oil, cod liver oil and anchovy oil, in particular menhaden oil.

Typical L-arginine and L-ornithine precursors, suitable for the purpose of the invention include small peptides rich in L-arginine and L-ornithine resp. The L-arginine and L-ornithine may be in free form or in salt form, e.g. a salt with phosphoric acid, citric acid, tartaric acid, fumaric acid, adipic acid or lactic acid.

The supplement is administered in an immune stimulatory aggregate amount during a period of time sufficient to trigger the enhanced immune response.

The daily amount of component (a) i.e. omega-3 PUFAs and of component (b) to be supplied to attain the desired effect will depend on the duration (days) of treatment, and of course on other factors such as the particular patient to be treated.

The supplement should advantageously be administered, e.g. 3 to 4 times per day, all over a period of 3 days or longer, e.g. from 3 to 6 days.

For adults, the total amount of omega-3 PUFAs supplied over that period of treatment should preferably not be below 15 g; the total amount of L-arginine and/or L-ornithine supplied by component (b) to adults over that period of treatment should conveniently not be below 60 g.

Administration of a daily amount of component (a) in the range of from 2 to 5 g in association with component (b) supplying from 7.5 to 20 g L-arginine and/or L-ornithine will in general suffice to attain the desired effect.

Higher amounts may, of course, be administered.

For use according to the method of the invention, the supplement may, and will preferably comprise further ingredients.

Examples of ingredients having a favourable effect on the immune response and/or the resistance to infection upon surgery, are, independently from each other omega-6 PUFAs (component c) and the pyrimidine and purine bases of nucleotides, hereinafter designated nucleobases (component d).

For the purpose of the invention the omega-6 PUFAs may be in free acid form or in a form suitable for the physiological supply of omega-6 PUFAs, e.g. in triglyceride form. Examples of omega-6 PUFAs particularly appropriate for use according to the invention, include linoleic acid and arachidonic acid (ETA), linoleic acid being most preferred. Examples of suitable omega-6 PUFA sources are known in the art. They include vegetable oils. Preferred are omega-6 PUFA sources having a high linoleic acid content such as safflower oil, sunflower oil, soya oil, cotton oil and corn oil.

For adults, the total amount of omega-6 PUFAs supplied over the period of treatment should preferably not be below 10 g.

Administration of a daily amount of component (c) in the range of from 1.5 to 5.0 g will in general suffice to attain a favourable effect.

In general it will be advantageous to use an amount of component (a) in excess of the amount of component (c) employed.

Components (a) and (c) may also be employed in admixture with other fatty acids, including omega-9 PUFAs. A preferred natural source for such fatty acid mixtures are fish oils. For taste and other reasons, the fish oils will, in oral application forms, preferably be used in encapsulated form.

Nucleobase sources suitable for use in the composition of the invention comprise or consist of natural nucleobases, nucleosides, nucleotides, RNA, DNA, equivalents thereof and/or mixtures comprising one or more of these compounds.

Natural nucleobases include the purines adenine and guanine as well as the pyrimidines cytosine, thymine and uracil. Where the nucleobase source is in the form of free nucleobases, it is preferably uracil.

Natural nucleosides include the ribose nucleosides adenosine, guanosine, uridine and cytidine and the deoxyribose nucleosides deoxyadenosine, deoxyguanosine, deoxythymidine and deoxycytidine.

Natural nucleotides include phosphate esters of natural nucleosides, such as the monophosphates adenylate (AMP), guanylate (GMP), uridylate (UMP), cytidylate (CMP) deoxythymidylate (dTMP) deoxycytidylate (dCMP), and diphosphates and triphosphates of natural nucleosides such as ADP and ATP.

A purified nucleobase source, such as yeast, is preferred. However, other sources such as meat and the like may be used.

For adults, the total amount of RNA supplied over the period of treatment should preferably not be below 5 g.

Administration of a daily amount of RNA in the range of from 0.7 g to 2 g will in general suffice to attain a favourable effect. Equivalent amounts of other nucleobase sources may be used. For the purpose of this invention one weight unit of nucleobase is regarded to be equivalent with 2.5 to 3.0 weight units of RNA, DNA, nucleosides or nucleotides.

The compositions of the invention may be formulated in a form suitable for parenteral or enteral administration. They are particularly appropriate for enteral use, e.g. for oral administration, nasal administration and/or tube feeding. Such compositions are conveniently administered in the form of an aqueous liquid. The compositions of the invention suitable for enteral application are accordingly preferably in aqueous form or in powder form, whereby the powder is conveniently added to water prior to use. For use as tube feeding, the amount of water to be added will i.a. depend on the patient's fluid requirements and condition.

The composition of the invention may comprise vitamins, mineral, trace elements as well as additional nitrogen, carbohydrate and fatty acid sources.

It comprises conveniently also nutritionally acceptable fibre, preferably soluble fibre. The term soluble fibre as used herein refers to fibers which are able to substantially undergo fermentation in the colon to produce short chain fatty acids. Examples of suitable soluble fibers include pectin, guar gum, locust bean gum, xanthan gum. They may be hydrolysed or not. For adults the total amount of soluble fibre per day will conveniently lie in the range of from 3 to 30 g/day. The composition of the invention is primarily intended for use as a supplement. The amount of energy supplied by it should in such case not be too excessive, in order not to unnecessarily suppress the patients appetite. The supplement should conveniently comprise energy sources in an amount supplying from 600 to 1500 Kcal/day. The contribution of the nitrogen source, carbohydrate source and lipid source to the total daily caloric may vary within wide ranges. In preferred compositions of the invention the carbohydrate source provides for 40 to 70% of the total energy supply and, the nitrogen and fatty acid source each for 15 to 30% of the total energy supply of the composition.

Examples of suitable nitrogen sources include nutritionally acceptable proteins such as caseinates, or protein hydrolysates.

Examples of suitable carbohydrate sources include maltodextrins.

Examples of suitable fatty acid energy supply sources include triglyceride sources.

Examples of vitamins suitable for incorporation in the composition of the invention include vitamin A, vitamin D, vitamin E, vitamin K, vitamin C, folic acid, thiamin, riboflavin, vitamin $B_6$, vitamin $B_{12}$, niacin, biotin and panthotenic acid in pharmaceutically acceptable form.

Examples of mineral elements and trace elements suitable for incorporation in the composition of the invention include sodium, potassium, calcium, phosphorous, magnesium, manganese, copper, zinc, iron, selenium, chromium and molybdenum in pharmaceutically acceptable form.

In particular, the compositions of the invention will preferably comprise beta-carotene (vitamin A), vitamin E, vitamin C, thiamine, vitamin $B_{12}$, choline selenium and zinc in pharmaceutically acceptable form.

The diet of the invention is indicated for improving the immune response system of patients and acts as a pre-operative diet.

It is also indicated for use prior to operative procedures, to improve the resistance to infection of patients due to undergo surgery.

It is particularly indicated for use following major operative procedures, i.e. including any operative procedure requiring general anesthesia such as cardiac by pass surgery and major upper gastrointestinal surgery.

The composition of the invention may be obtained in a manner known per se, e.g. by admixing the ingredients.

The following examples illustrate the invention:

Example 1

Powder form—(1 sachet—74 g) Energy/sachet: 302.8 Kcal.

| Nitrogen source | g | 16.7 |
|---|---|---|
| caseinates | g | (13.0) |
| L-Arginine | g | (3.74) |
| Fatty Acid Source | g | 8.3 |
| essential fatty acids | g | (0.94) |
| omega-6 PUFAs | g | (0.74) |
| omega-3 PUFAs | g | (1.00) |
| Carbohydrate Source (Maltodextrines) | g | 40.2 |
| Gummi arabicum | g | 3.0 |
| Yeast RNA | g | 0.38 |
| Sodium | mg | 320 |
| Potassium | mg | 402 |
| Calcium | mg | 240 |
| Magnesium | mg | 80 |
| Phosphorous | mg | 216 |
| Chloride | mg | 480 |
| Iron | mg | 3.6 |
| Copper | mg | 0.5 |
| Manganese | mg | 0.6 |
| Zinc | mg | 4.5 |
| Fluor | mg | 0.5 |
| Iodine | mcg | 45.0 |
| Chromium | mcg | 30.0 |
| Molybedenum | mcg | 60.0 |
| Selenium | mcg | 14.0 |
| Vit. A | mg | 0.30 |
| Vit. D | mcg | 2.00 |
| Vit. E | mg | 4.00 |
| Vit. $K_1$ | mcg | 20.00 |
| Vit. $B_1$ | mg | 0.36 |
| Vit. $B_2$ | mg | 0.52 |
| Vit. $B_6$ | mg | 0.43 |
| Vit. $B_{12}$ | mcg | 1.20 |
| Vit. C | mg | 20.00 |
| Biotin | mcg | 30.00 |
| Folic Aciol | mcg | 60.00 |
| Niacinamide | mg | 4.80 |
| Pantothenic acid | mg | 2.40 |
| Cholic acid | mg | 80.00 |

Example 2

Influence of a pre-operative oral nutritional support on serum and cellular fatty acid composition and on neutrophil functions from patients with major surgery The serum and fatty acid composition and the neutrophil functions from forty patients (average score and age) admitted for major surgery, are analyzed in a randomized placebo controlled double blind study, 5 days before and at the day of the surgery as well as 1 and 7 days after the operation. The patients were divided into two groups. One group received orally an aqueous solution of the composition of Example 1 (in an average amount of 1000 Kcals per day; given in 3 to 4 servings (drinks) of 300 Kcals each during the last 5 days preceding the operation); the other group an isocaloric control nutrition (placebo) having essentially the same composition as that of Example 1 except that 1 sachet placebo of 74 g comprises

| | | |
|---|---|---|
| • nitrogen source | g | 13.00 |
| | | (all as caseinate no L-Arginine) |
| • fatty acid sources | g | 8.33 |
| essential fatty acids | g | (3.04) |
| omega-6 PUFAs | g | (3.00) |
| omega-3 PUFAs | g | (—) |
| • Carbohydrates | g | (43.94) |

(hereinafter referred to as Standard Composition)

(a) Biopsies from the liver, small bowel mucosa and the gastrointestinal tumor were taken from all patients intraoperatively. These tissues and serum lipids were assayed for their fatty acid composition by gas chromatography.

In the group with the supplement of the invention, all examined tissues showed a significantly higher content of EPA, that was accompanied by an increase in the serum lipid EPA concentration.

TABLE I

| Eicosapentaenoic acid (EPA) - in weight % | | |
|---|---|---|
| | Comp. I[1] mean | Comp. S[2] mean |
| liver | 1.26* | 0.35 |
| mucosa | 1.00* | 0.26 |
| tumor | 0.76* | 0.30 |
| serum lipids | 2.53* | 1.11 |

[1]after treatment with the Composition of Example 1
[2]after treatment with the Standard Compositions defined hereinabove
*$p < 0.05$ The data show a significant modulation of the eicosanoid release after preoperative oral treatment with the supplement of the invention. The results demonstrate that preoperative modulation of membrane fatty acid profiles by dietary manipulation offers the possibility to shift the postoperative release of eicosanoids towards components with lower inflammatory potential.

(b) Neutrophils were isolated from the peripheral blood and stimulated with the Ca-ionophor A23187 (7.3 uM). The capacity of the respective neutrophils to generate leukotrienes was analyzed by RP-HPLC. Neutrophils from the group treated with the composition of the invention generated significantly higher amounts of LTB5 (mean values 6.6 ng/I×10⁷ cells) compared to placebo (2.9 ng/I at the day of the surgery (day 0; p<0.05). In contrast, the capacity of neutrophils to produce LTB4 was not significantly different in both patients groups at the day of the surgery and 7 days after surgery.

The LTB5 release by Ca-ionophor stimulated leukocyte cultures was determined 5 days preoperatively, on the day of operation and on the first and seventh postoperative day.

The elevated LTB5 level remained significantly enhanced for seven days after the supplementation was stopped. In the placebo group the LTR5-release remained unchanged.

In the following Table Day 0 means the day of the operation, Day -5 weeks 5 days before, Day 1 means 1 day after the operation etc.

| | LTB4 (ng/ml) | | LTB5 (ng/ml) | |
|---|---|---|---|---|
| Day | Comp. I[1] mean | Comp. S[2] mean | Comp. I[1] mean | Comp. S[2] mean |
| -5 | 56.4 | 56.3 | 4.02 | 3.04 |
| 0 | 49.2 | 48.5 | 6.60* | 2.86 |
| 1 | 54.7* | 77.4 | 7.32* | 2.63 |
| 7 | 39.1 | 53.0 | 5.21 | 4.64 |

*$p < 0.05$
[1]after treatment with the Composition of Example 1
[2]after treatment with the Standard Compositions as defined hereinabove.

(c) Determination of NK-cells, Suppressor cells (CD8), activated T cells (CD3, and IL-1α cells confirm that postoperative immundepression is significantly less expressed following treatment with Composition I compared to Composition S (Standard)-Tables III and IV.

TABLE III

| | NK-cells (cells/ml) | | Suppressor CD8 cells (cells/ml) | |
|---|---|---|---|---|
| Day | Comp. I mean | Comp. S mean | Comp. I mean | Comp. S mean |
| -5 | 233 | 217 | 523 | 548 |
| 0 | 257 | 229 | 607 | 569 |
| 1 | 169* | 85 | 443* | 323 |
| 7 | 176 | 116 | 506 | 455 |
| 14 | 200 | 143 | 507 | 507 |

TABLE IV

| | Activated T cells (cells/ml) | | IL-1α (cells/ml) | |
|---|---|---|---|---|
| Day | Comp. I mean | Comp. S mean | Comp. I mean | Comp. S mean |
| -5 | 216 | 201 | 131 | 166 |
| 0 | 236 | 219 | 154 | 168 |
| 1 | 184* | 110 | 118* | 57 |
| 7 | 199 | 167 | 146* | 69 |
| 14 | 210 | 218 | 166* | 84 |

*$p < 0.05$

I claim:

1. A method of improving the immune response and/or resistance to infection of a patient following surgery comprising treating said patient pre-operatively with a diet supplement comprising an immunostimulating effective aggregate amount of (a) omega-3 PUFAs and (b) L-arginine, L-ornithine, an L-arginine or L-ornithine precursor, or a mixture thereof.

2. The method of claim 1, which comprises including an effective amount of omega-6 PUFAs.

3. The method of claim 1, which comprises administering the omega-3 PUFAs in the form of fish oil.

4. The method of claim 2, which comprises administering the omega-3 and omega-6 PUFAs in the form of fish oil.

5. The method of claim 3, wherein the fish oil is in encapsulated form.

6. The method of claim 4, wherein the fish oil is in encapsulated form.

7. The method of claim 1, which comprises including an effective amount of a nucleobase source.

8. A method of improving the immune response and/or resistance to infection of a patient following surgery comprising treating said patient pre-operatively with a diet supplement consisting essentially of an immunostimulating effective aggregate amount of (a) omega-3 PUFAs and (b) L-arginine, L-ornithine, an L-arginine or L-ornithine precursor, or a mixture thereof.

9. A method of improving the immune response and/or resistance to infection of a patient following surgery comprising treating said patient pre-operatively with a diet supplement consisting essentially of an immunostimulating effective aggregate amount of (a) omega-3 PUFAs, (b) L-arginine, L-ornithine, an L-arginine or L-ornithine precursor, or a mixture thereof, and (c) omega-6 PUFAs.

10. A method of improving the immune response and/or resistance to infection of a patient following surgery comprising treating said patient pre-operatively with a diet supplement consisting essentially of an immunostimulating effective aggregate amount of (a) omega-3 PUFAs, (b) L-arginine, L-ornithine, an L-arginine or L-ornithine precursor, or a mixture thereof, and (d) a nucleobase source.

* * * * *

UNITED STATES PATENT AND TRADEMARK OFFICE
CERTIFICATE OF CORRECTION

PATENT NO. : 5,731,290
DATED : MARCH 24, 1998
INVENTOR(S) : HEINZ SCHNEIDER

It is certified that error appears in the above-identified patent and that said Letters Patent is hereby corrected as shown below:

Title page, Item: [73] should read:

-- [73] Assignee: Novartis Nutrition AG, Berne, Switzerland --.

Signed and Sealed this

Twenty-seventh Day of April, 1999

Attest:

Q. TODD DICKINSON

Attesting Officer

Acting Commissioner of Patents and Trademarks